(12) United States Patent
Chen et al.

(10) Patent No.: US 12,296,195 B2
(45) Date of Patent: May 13, 2025

(54) RADIATION THERAPY SYSTEM, AND OPERATION PROCEDURE OF POSITIONING DEVICE THEREOF

(71) Applicant: NEUBORON THERAPY SYSTEM LTD., Fujian (CN)

(72) Inventors: Wei-Lin Chen, Fujian (CN); Qiu-Ping Gong, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 272 days.

(21) Appl. No.: 17/732,727

(22) Filed: Apr. 29, 2022

(65) Prior Publication Data

US 2022/0266061 A1  Aug. 25, 2022

Related U.S. Application Data

(63) Continuation of application No. PCT/CN2020/118385, filed on Sep. 28, 2020.

(30) Foreign Application Priority Data

Oct. 29, 2019  (CN) .......................... 201911034270.3

(51) Int. Cl.
*A61N 5/10* (2006.01)
*A61B 6/04* (2006.01)

(52) U.S. Cl.
CPC ......... *A61N 5/1049* (2013.01); *A61N 5/1077* (2013.01); *A61N 2005/105* (2013.01); *A61N 2005/1059* (2013.01)

(58) Field of Classification Search
None
See application file for complete search history.

(56) References Cited

U.S. PATENT DOCUMENTS 5,818,007 A * 10/1998 Itatsu .................. B23K 11/314
219/86.25
2006/0255220 A1  11/2006 Skripps
(Continued)

FOREIGN PATENT DOCUMENTS

| CN | 104707260 A | 6/2015 |
| CN | 105011955 A | 11/2015 |

(Continued)

OTHER PUBLICATIONS

International Search Report of PCT/CN2020/118385, Jan. 11, 2021.

*Primary Examiner* — Eliza W Osenbaugh-Stewart
(74) *Attorney, Agent, or Firm* — Troutman Pepper Locke LLP; Tim Tingkang Xia, Esq.

(57) ABSTRACT

Provided is an operation procedure of a positioning device of a radiation therapy system. The radiation therapy system includes a radiation generation device used to generate therapeutic radiation, an irradiation chamber used to accommodate an irradiation subject receiving the radiation, a management chamber used to achieve irradiation control, and a support device used to transport and support the irradiation subject. The support device includes a support member supporting the irradiation subject, an adjustment assembly for adjusting a spatial position of the support member, and a joining assembly fixedly connecting the support member and the adjustment assembly together in a detachable manner. The support member at least includes a first support member and a second support member having a different size and/or shape from the first support member. The invention allows switching between support members having different sizes and/or shapes according to an actual use requirement.

14 Claims, 4 Drawing Sheets

(56) References Cited

U.S. PATENT DOCUMENTS

| | | |
|---|---|---|
| 2007/0039101 A1 | 2/2007 | Luginbuhl et al. |
| 2007/0238949 A1 | 10/2007 | Wang et al. |
| 2014/0033432 A1 | 2/2014 | Marle |
| 2018/0177470 A1 | 6/2018 | Suga et al. |

FOREIGN PATENT DOCUMENTS

| | | |
|---|---|---|
| CN | 104307113 B | 1/2017 |
| CN | 108653935 A | 10/2018 |
| CN | 110064133 A | 7/2019 |
| CN | 209451161 U | 10/2019 |
| CN | 211410741 U | 9/2020 |
| JP | S63189129 A | 8/1988 |
| JP | S6485675 A | 3/1989 |
| JP | H0352409 U | 5/1991 |
| JP | H05281359 A | 10/1993 |
| JP | H09220674 A | 8/1997 |
| JP | 2007502166 A | 2/2007 |
| JP | 2016209992 A | 12/2016 |
| JP | 2019177212 A | 10/2019 |
| TW | 201247176 A | 12/2012 |
| WO | 2017003816 A1 | 1/2017 |

* cited by examiner

RADIATION THERAPY SYSTEM, AND OPERATION PROCEDURE OF POSITIONING DEVICE THEREOF

CROSS-REFERENCE TO RELATED PATENT APPLICATION

This application is a continuation application of International Application No. PCT/CN2020/118385, filed on Sep. 28, 2020, which claims priority to Chinese Patent Application No. 201911034270.3, filed on Oct. 29, 2019, the disclosures of which are hereby incorporated by reference.

FIELD

The present disclosure relates to a radioactive radiation irradiation system, and in particular to a radiation therapy system and operation procedure of a positioning device thereof.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

With the development of atomic science, radiation therapy, such as Cobalt 60, linear accelerator and electron beam, etc., has become one of the main means of cancer treatment. During the radiation therapy, the patient needs to be continuously irradiated with a beam for a certain period of time, during which the patient needs to be fixed on a support member and transferred to a predetermined position by an adjustment component connected with the support member. In an existing treatment apparatus, the support member has one single shape and size, which cannot be adaptable to patients having different body shapes and different tumor positions. In addition, there are other facilities in an irradiation chamber, and when movement positions of support members with certain shapes and sizes are interfered, irradiation cannot be carried out with an optimal irradiation point and an optimal irradiation angle, thus reducing the therapeutic effect.

SUMMARY

In order to solve the above problem, a first aspect of the disclosure provides a radiation therapy system that may be adaptable to patients having different body shapes and different tumor positions, the radiation therapy system includes a radiation generation device configured to generate therapeutic radiation, an irradiation chamber configured to accommodate a to-be-irradiated object subjecting to irradiation of the radiation, a management chamber configured to perform irradiation control, and a support device configured to transport and support the to-be-irradiated object, and the support device includes a support member configured to support the to-be-irradiated object, an adjustment component configured to adjust a spatial position of the support member, and a clamping component configured to fixedly connect the support member and the adjustment component together in a detachable manner, and the support member includes at least a first support member and a second support member having a different size and/or shape from the first support member.

Further, the clamping component may include a first positioning block disposed on the support member, a second positioning block disposed on the adjustment component, and a locking member configured to lock or release the second positioning block relative to the first positioning block.

Further, the support member may include a first surface disposed towards the first positioning block, the first positioning block is disposed on the first surface and is provided with a limiting slot for a second limiting block to be inserted along a first direction parallel to the first surface, a reserved slot communicated with the limiting slot along a second direction perpendicular to the first surface such that the adjustment component passes through it, and a locking hole communicated with the limiting slot and matched with the locking member, and the limiting slot penetrates through one of faces of the first positioning block along the first direction to form an insertion opening, and the second positioning block is inserted into the limiting slot from the insertion opening along the first direction.

Further, the locking member may include a mounting part fixedly connected with the second positioning block, a locking pin insertable into or movable out of the locking hole, and a first driving member configured to drive the locking pin to insert into or move out of the locking hole, and the locking hole penetrates through the first positioning block and communicates with the limiting slot.

Further, the support device may further include a detection component configured to detect whether the locking pin is moved in place so as to determine whether the support member and the adjustment component are effectively connected together.

Further, the radiation therapy system may further include a positioning device configured to control a movement trajectory of the support member.

Further, the positioning device may include a laser positioning component, an alignment component, an optical verification component, a distance measuring component, a driving component configured to drive the adjustment component to move so as to drive the support member to move, and a control component configured to control a movement trajectory of the adjustment component.

Further, the alignment component may include a positioning frame with an adjustable relative position with respect to the support member, a support rod connected between the support member and the positioning frame to adjust the relative position of the positioning frame with respect to the support member, and a locking member configured to lock the relative position of the positioning frame with respect to the support member. Further, the radiation therapy system may further include a transmission device disposed between the adjustment component and the support member such that the support member is movable relative to the adjustment component.

Further, the transmission device may include a substrate fixedly connected with the adjustment component, a guiding member disposed on the substrate, a slider slidable relative to the guiding member, a driving block configured to drive the slider to move, and a second driving member configured to drive the driving block to move.

Further, the irradiation chamber may be provided with a collimator allowing emission of the radiation, the radiation emits from an exit of the collimator and defines a beam axis with an optimal treatment point; the laser positioning component includes at least two laser emitters disposed at different orientations, lasers emitted by the at least two laser emitters have a laser intersection point, and an optimal irradiation point of the to-be-irradiated object, the laser intersection point and the optimal treatment point coincide during treatment.

Further, the positioning frame may have a positioning point coinciding with the optimal irradiation point of the to-be-irradiated object during treatment.

Further, the optical verification component may include a CCD camera as well as an image processing and identifying module.

A second aspect of the disclosure provides an operation procedure of the positioning device: S1: the laser positioning component marks the optimal treatment point by using the laser intersection point, and the optimal treatment point corresponds to a coordinate (X, Y, Z) and a relative angle $\alpha$; S2: the CCD camera takes a picture of the laser intersection point to obtain a photo, and the image processing and identifying module analyzes and marks the laser intersection point in the photo; S3: the to-be-irradiated object is located on the support member, and a medical staff aligns the positioning point of the positioning frame with the optimal irradiation point of the to-be-irradiated object, and then the medical staff locks a position of the positioning frame by using the locking member; S4: the CCD camera takes a picture in which the to-be-irradiated object is located on the support member and the alignment component is adjusted in place to obtain a photo, then the image processing and identifying module analyzes and records a coordinate (X1, Y1) and a relative angle $\alpha 1$ of a positioning point of the alignment component in the photo, and then the image processing and identifying module calculates a coordinate difference value between the positioning point and the laser intersection point: $X0=X1-X, Y0=Y1-Y, \alpha 0=\alpha 1-\alpha$; S5: the control component determines the movement trajectory of the adjustment component through calculation according to the coordinate difference value obtained from the optical verification component, and then the control component controls the driving component to drive the adjustment component to move, such that the optimal irradiation point of the to-be-irradiated object on the support member is moved to a position corresponding to a coordinate (x, y) and the relative angle $\alpha$;

S6: the distance measuring component detects a distance between the positioning point and the laser intersection point; and S7: the control component determines the movement trajectory of the adjustment component through calculation according to data obtained from the distance measuring component, and then the control component controls the drive component to drive the adjustment component to move, such that the optimal irradiation point of the to-be-irradiated object on the support member is moved to the optimal treatment point, that is, a position corresponding to the coordinate (X, Y, Z) and the relative angle $\alpha$, for treatment.

A third aspect of the disclosure provides an operation procedure of the positioning device: S1: the laser positioning component marks the optimal treatment point by using the laser intersection point, and the optimal treatment point corresponds to a coordinate (X, Y, Z) and a relative angle $\alpha$; S2: the CCD camera takes a picture of the laser intersection point to obtain a photo, and the image processing and identifying module analyzes and marks the laser intersection point in the photo; S3: the to-be-irradiated object is located on the support member, and a medical staff aligns the positioning point of the positioning frame with the optimal irradiation point of the to-be-irradiated object, and then the medical staff locks a position of the positioning frame by using the locking member; S4: the CCD camera takes a picture in which the to-be-irradiated object is located on the support member and the alignment component is adjusted in place to obtain a photo, then the image processing and identifying module analyzes and records a coordinate (X1, Y1) and a relative angle $\alpha 1$ of a positioning point of the alignment component in the photo, and then the image processing and identifying module calculates a coordinate difference value between the positioning point and the laser intersection point: $X0=X1-X, Y0=Y1-Y, \alpha 0=\alpha 1-\alpha$; S5: the distance measuring component detects a distance between the positioning point and the laser intersection point; and S6: the control component determines the movement trajectory of the adjustment component through calculation according to data obtained from the optical verification component and the distance measuring component, and then the control component controls the driving component to drive the adjustment component to move, such that the optimal irradiation point of the to-be-irradiated object on the support member is moved to the optimal treatment point, that is, a position corresponding to the coordinate (X, Y, Z) and the relative angle $\alpha$.

Compared with the related art, the technical solution described in the embodiment has the following beneficial effects: the clamping component may fixedly connect the support members having different sizes and/or shapes to the adjustment component in a detachable manner, therefore, the radiation therapy system of the disclosure may switch between support members having different shapes and/or sizes according to different usage requirements, such that the radiation therapy system may be adaptable to patients having different body shapes and different tumor positions.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Radiation therapy is a common means for cancer treatment, as shown in FIGS. 1 to 8, a radiation therapy system configured to perform radiation therapy includes a radiation generation device 1 configured to generate therapeutic radiation, an irradiation chamber 2 configured to accommodate a to-be-irradiated object subjecting to irradiation of the radiation, a management chamber 3 configured to perform irradiation control, and a support device 4 configured to transport and support a patient, and a positioning device configured to control a movement trajectory of the support device 4.

Figure 3:
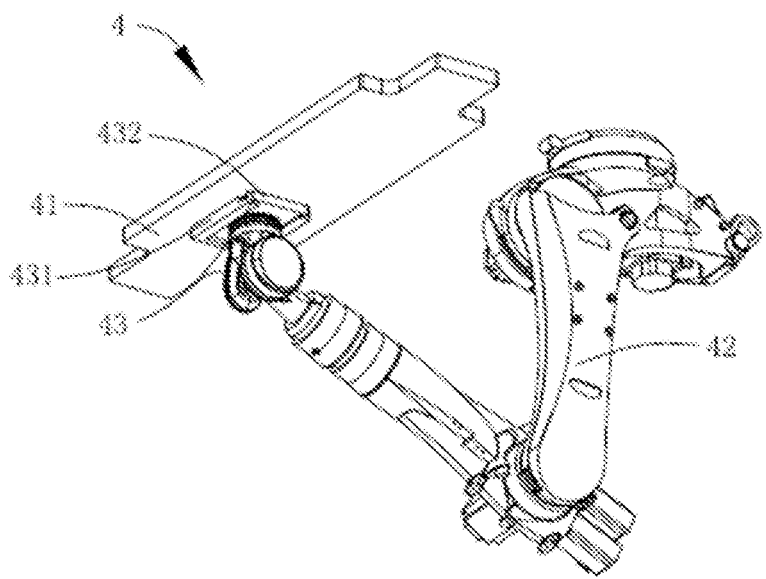
FIG. 3 is a schematic perspective view of a support device without mounting a transmission device of a radiation therapy system according to the disclosure.

Referring to FIG. 3, the support device 4 includes a support member 41 configured to support the patient, an adjustment component 42 configured to adjust a spatial position of the support member 41, and a clamping component 43 configured to fixedly connect the support member 41 and the adjustment component 42 together in a detachable manner.

The support member 41 corresponds to multiple types of support members according to different shapes and/or sizes, such as a plated-shaped first support member 41' and a chair-shaped second support member 41". Each of the first support member 41' and the second support member 41" may be provided with multiple size specifications to be adaptable to patients having different body shapes and different tumor positions. For example, a patient requires a certain irradiation angle, while the current support member 41 cannot be adjusted in place because of an interference of its shape and/or size with other devices of the irradiation chamber 2, then it may be considered to switch the current support member 41 to a support member 41 with another shape and/or size to realize adjustment of the irradiation angle. Or, when some parts of the patient, such as back side of the head, cannot be irradiated while the patient lies down, a better therapeutic effect may be achieved by using a support chair to support the patient.

Figure 4:
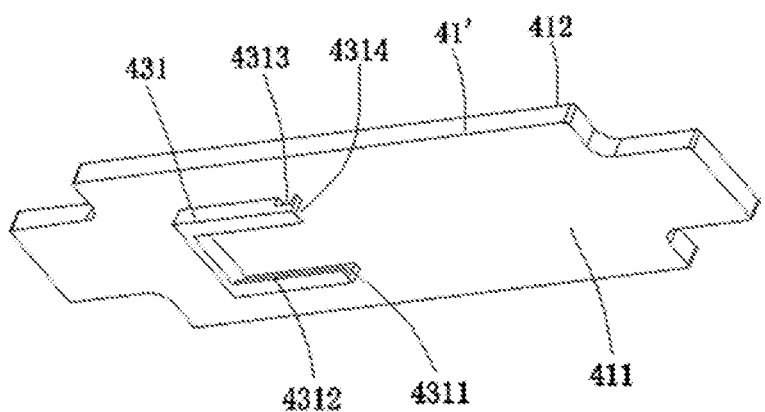
FIG. 4 is a schematic perspective view of a plate-shaped support member and a first positioning block of a radiation therapy system according to the disclosure.

Referring to FIG. 4, the support member 41 includes a first surface 411 configured to mount the clamping component 43 and a second surface 412 configured to support the patient. The adjustment component 42 may drive the support member 41 to move in six degrees of freedom.

The clamping component 43 includes a first positioning block 431 disposed on the first surface 411 of the support member 41, a second positioning block 432 disposed on the adjustment component 42, and a locking member 433 disposed on the second positioning block 432 and configured to lock or release the second positioning block 432 relative to the first positioning block 431. In particular, the first positioning block 431 is provided with a limiting slot 4311 for the second positioning block 432 to be inserted along a first direction parallel to the first surface 411, a reserved slot 4312 communicated with the limiting slot 4311 along a second direction perpendicular to the first surface 411, and a locking hole 4313 communicated with the limiting slot 4311 and matched with the locking member 433. The limiting slot 4311 penetrates through one face of the first positioning block 431 along the first direction to form an insertion opening 4314, and the second positioning block 432 is inserted into the limiting slot 4311 from the insertion opening 4314 along the first direction.

The first direction along which the second positioning block 432 is inserted into the limiting slot 4311 is defined as a front-back direction, the second direction perpendicular to the first surface 411 is defined as an up-down direction, and a direction orthogonal to both the front-back direction (the first direction) and the up-down direction (the second direction) is defined as a left-right direction. The limiting slot 4311 communicates with the reserved slot 4312 along the up-down direction and penetrates the first positioning block 431 along a direction away from the support member 41, and the adjustment component 42 penetrates through the reserved slot 4312 and connects with the second positioning block 432. In the left-right direction, a size of the reserved slot 4312 is smaller than a size of the limiting slot 4311 and a size of the second positioning block 432, so that the second positioning block 432 cannot depart from the limiting slot 4311 along the up-down direction.

Figure 5:
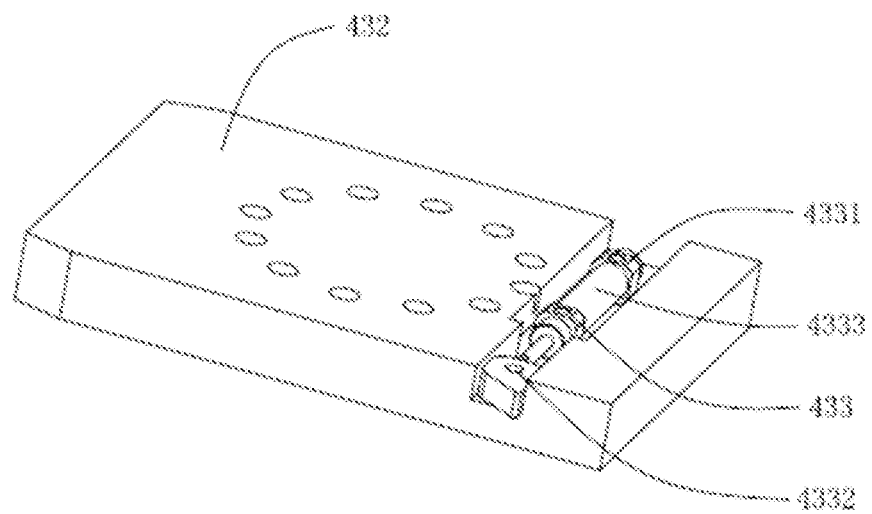
FIG. 5 is a schematic perspective view of a second positioning block and a locking member of a radiation therapy system according to the disclosure.
Figure 6:
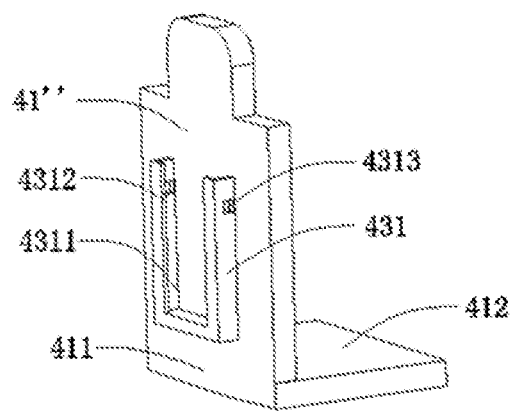
FIG. 6 is a schematic perspective view of a chair-shaped support member and a first positioning block of a radiation therapy system according to the disclosure.

Referring to FIG. 5, the locking member 433 includes a mounting part 4331 fixedly connected with the second positioning block 432, a locking pin 4332 insertable into or movable out of the locking hole 4313, and a first driving member 4333 configured to drive the locking pin 4332 to insert into or move out of the locking hole 4313. The locking hole 4313 penetrates through the first positioning block 431 along the left-right direction and communicates with the limiting slot 4311, the locking pin 4332 is inserted into or moved out of the locking hole 4313 so as to selectively prevent the first positioning block 431 from moving relative to the first positioning block 431 along the front-back direction, while the limiting slot 4311 penetrates through only one of the faces of the first positioning block 431 along the front-back direction and the left-right direction parallel to the first surface 411, and when the locking pin 4332 is inserted into the locking hole 4313, movement of the second positioning block 432 relative to the first positioning block 431 along the front-back direction and the left-right direction is prevented, so that the adjustment component 42 and the support member 41 are fixedly connected together in a detachable manner.

In order to prevent a situation where the first positioning block 431 and the second positioning block 432 cannot be securely connected together since the locking pin 4332 isn't moved in place, the support device 4 further includes a detection component (not shown) configured to detect whether the locking pin 4332 is moved in place so as to determine whether the support member 41 and the adjustment component 42 are effectively connected together.

Figure 1:
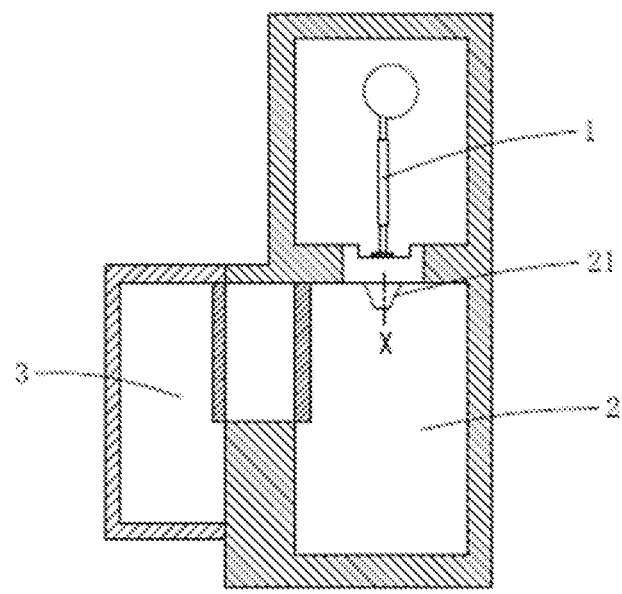
FIG. 1 is a top view of a radiation therapy system with a support device and a positioning device removed according to the disclosure.
Figure 2:
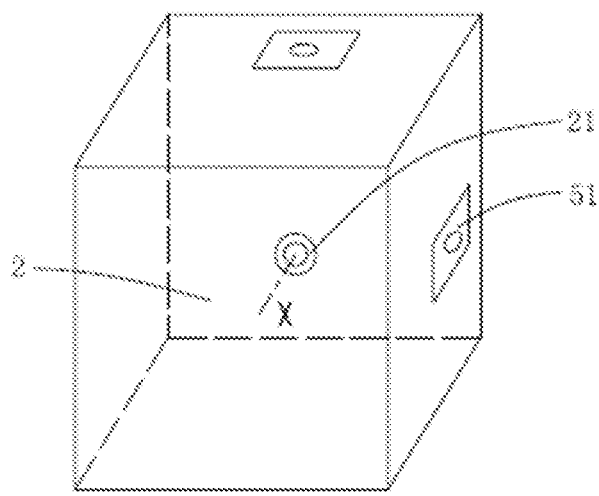
FIG. 2 is a schematic perspective view of an irradiation chamber of a radiation therapy system according to the disclosure.
Figure 7:
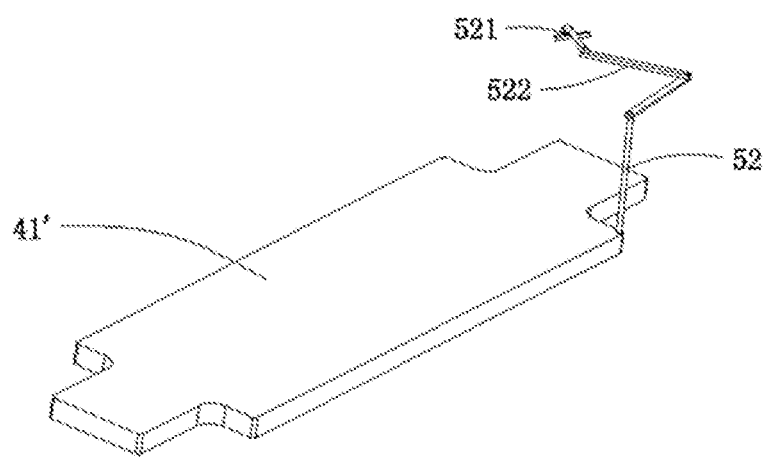
FIG. 7 is a schematic perspective view of a plate-shaped support member and an alignment component of a radiation therapy system according to the disclosure.

As shown by combining FIG. 2 with FIG. 7, the positioning device includes a laser positioning component 51, an alignment component 52, an optical verification component (not shown), a distance measuring component (not shown), a driving component (not shown) configured to drive the adjustment component 42 to move so as to drive the support member 41 to move, and a control component (not shown) configured to control a movement trajectory of the adjustment component 42.

The adjustment component 42 may, under the driving of the driving component, drive the support member 41 to move in six degrees of freedom.

The irradiation chamber 2 is provided with a collimator 21 allowing emission of the radiation generated by the radiation generation device 1, the radiation emits from an exit of the collimator 21 and defines a beam axis X coinciding with a center line of the collimator 21. On the beam axis X, an optimal treatment point is located at a position of 15-20 CM away from the exit of collimator 21, and an optimal irradiation point of the patient needs to coincide with the optimal treatment point during treatment.

Referring to FIG. 2, the laser positioning component 51 includes at least two laser emitters disposed at different orientations, the at least two laser emitters are disposed on two different walls of the irradiation chamber 2 respectively, and one of the at least two laser emitters is usually disposed on the top wall of the irradiation chamber 2. Lasers emitted by the at least two laser emitters have one single laser intersection point coinciding with the aforementioned optimal treatment point.

Referring to FIG. 7, the alignment component 52 includes a positioning frame 521 with an adjustable relative position with respect to the support member 41, a support rod 522 connected between the support member 41 and the positioning frame 521 to adjust the relative position of the positioning frame 521 with respect to the support member 41, and a locking member (not shown) configured to lock the relative position of the positioning frame 521 with respect to the support member 41, and the positioning frame 521 has a positioning point. In the embodiment disclosed in the disclosure, the support rod 522 has three rods which are rotatable relatively, and the relative position of the positioning frame 521 with respect to the support member 41 is adjusted by adjusting a relative angle and position between any two of the three rods. After the patient lies or sits on the support member 41, a medical staff aligns the positioning point of the positioning frame 521 with the optimal irradiation point of the patient by adjusting the support rod 522, and then locks the position of the positioning frame 521 by the locking member.

The optical verification component includes a CCD camera as well as an image processing and identifying module.

The distance measuring component detects a distance between the positioning point and the laser intersection point along a direction perpendicular to the second surface 412 of the support member 41, and the distance measuring component may be a commonly used ranging instrument, such as a laser rangefinder, etc.

The CCD camera is configured to take a relevant picture, and the image processing and identifying module is configured to analyze coordinate and relative angle of a certain point in the picture taken by the CCD camera.

An operation procedure of the positioning device is as follows:

S1: the laser positioning component 51 marks the optimal treatment point by using the laser intersection point, and the optimal treatment point corresponds to a coordinate (X, Y, Z) and a relative angle $\alpha$;

S2: the CCD camera takes a picture of the laser intersection point to obtain a photo, and the image processing and identifying module analyzes and marks the laser intersection point in the photo;

S3: the patient lies or sits on the support member 41, and a medical staff aligns the positioning point of the positioning frame 521 with the optimal irradiation point of the patient by adjusting the support rod 522, and then the medical staff locks a position of the positioning frame 521 by using the locking member;

S4: the CCD camera takes a picture in which the patient lies or sits on the support member 41 and the alignment component 52 is adjusted in place to obtain a photo, then the image processing and identifying module analyzes and records a coordinate (X1, Y1) and a relative angle $\alpha 1$ of a positioning point of the alignment component 52 in the photo, and then the image processing and identifying module calculates a coordinate difference value between the positioning point and the laser intersection point: $X0=X1-X$, $Y0=Y1-Y$, $\alpha 0=\alpha 1-\alpha$;

S5: the control component determines the movement trajectory of the adjustment component 42 through calculation according to the coordinate difference value obtained from the optical verification component, and then the control component controls the driving component to drive the adjustment component 42 to move, such that the optimal irradiation point of the patient on the support member 41 is moved to a position corresponding to a coordinate (x, y) and the relative angle $\alpha$;

S6: the distance measuring component detects a distance between the positioning point and the laser intersection point along a direction perpendicular to the second surface 412 of the support member 41; and S7: the control component determines the movement trajectory of the adjustment component 42 through calculation according to data obtained from the distance measuring component, and then the control component controls the drive component to drive the adjustment component 42 to move, such that the optimal irradiation point of the patient on the support member 41 is moved to the optimal treatment point, that is, a position corresponding to the coordinate (X, Y, Z) and the relative angle $\alpha$, for treatment.

Before performing the operation S3, the support member 41 may be moved to a position close to the laser intersection point by visual inspection, the position is determined by the medical staff according to experience in combination with the patient's body shape, the optimal irradiation point, etc.

The operation S6 may be performed before the operation S5, in this case, the operations S5 and S7 are combined to directly adjust the support member 41 to the position corresponding to the coordinate (X, Y, Z) and the relative angle $\alpha$.

In the aforementioned operation procedure, a certain point on the adjustment component 42 is set as a coordinate origin, and of course, the coordinate origin may also be set at any other point.

In the embodiment disclosed in the disclosure, the positioning frame 521 is a cross-shaped positioning frame, and the positioning point is a cross-shaped intersection point. In other embodiments, the positioning frame 521 may be a V-shaped positioning frame, and the positioning point may be any marking point of any positioning frame.

Figure 8:
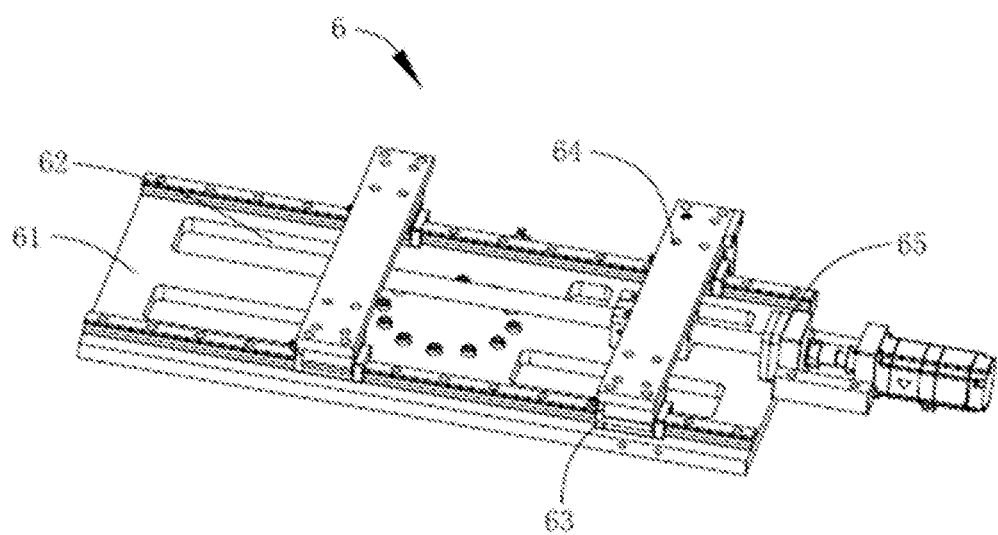
FIG. 8 is a schematic perspective view of a transmission device of a radiation therapy system according to the disclosure.

Referring to FIG. 8, since various devices exist in the irradiation chamber 2, the adjustment component 42 may interfere with these devices at some positions, which results in some limitation on the movement trajectory of the adjustment component 42, so that the optimal irradiation point of the patient cannot be moved to the optimal treatment point. In another embodiment of the disclosure, a transmission device 6 is disposed between the adjustment component 42 and the support member 41 such that the support member 41 is movable relative to the adjustment component 42 so as to ensure that the optimal irradiation point of the patient may be moved to the optimal treatment point to the maximum extent.

In the embodiment disclosed in the disclosure, the transmission device 6 is disposed between the second positioning block 432 and the adjustment component 42, and includes a substrate 61 fixedly connected with the adjustment component 42, a guiding member 62 disposed on the substrate 61, a slider 63 slidable relative to the guiding member 62, a driving block 64 connected between the slider 63 and the second positioning block 432, and a second driving member 65 configured to drive the driving block 64 to move.

The guiding member 62 are two spaced-apart guide rails disposed in parallel with each other, and the slider 63 is disposed across the guide rail; the driving block 64 is fixedly connected with the second positioning block 432 and is connected between the second driving member 65 and the slider 63; preferably, the second driving member 65 is a motor or an cylinder, and the second driving member 65 drives the drive block 64 to move so as to drive the slider 63 to move along a direction defined by the guiding member 62, and simultaneously, the driving block 64 drives the second positioning block 432 to move, so that the support member 41 moves on a trajectory predetermined by the guide member 62 relative to the adjustment component 42. Since the support member 41 and the adjusting component 42 may move relatively, the range of movement of the support member 41 may be increased by 30%, thereby increasing the range for treatment.

In the embodiments disclosed in the disclosure, the adjustment component 42 is a robotic arm, while in other embodiments, the adjustment component 42 may be provided as a bracket or the like.

In other embodiments, the driving block 64 may not be provided, and instead, the second positioning block 432 may be adopted to replace the driving block 64; in other embodiments, the transmission device 6 may be disposed between the support member 41 and the first positioning block 431; in addition, the transmission device 6 may also be disposed between the support member 41 and the first positioning block 431, in this case, the transmission device 6 may be disposed integrally with the first positioning block 431, and the transmission 6 is connected with the support member 41 in a manner that they may be quickly mounted and detached.

The disclosure adopts the clamping component 43 to quickly detach the support member 41 from the adjustment component 42 or mount them together, so that the size and shape of the support member 41 may be switched freely according to an actual use requirement, and thus the radiation therapy system may be adaptable to patients having different body shapes and different tumor positions, the irradiation range is increased for treatment, the efficiency is improved, and the time spent by an operator in the irradiation chamber 2 is reduced.

The support member 41 is automatically and rapidly moved in place by the positioning device, so as to improve the treatment efficiency and reduce the time spent by the operator in the irradiation chamber 2.

The transmission device 6 is provided between the support member 41 and the adjustment component 42, such that the support member 41 and the adjusting component 42 may move relatively, the range of movement of the support member 41 may be increased by 30%, thereby increasing the range for treatment.

In recent years, the application of neutron capture therapy as an effective means for cancer treatment has increased gradually. Among them, boron neutron capture therapy is the most common means. Neutrons for the boron neutron capture therapy may be supplied by a nuclear reactor or an accelerator. Preferably, the aforementioned radiation is a neutron beam, the radiation generation device 1 is a neutron beam generation device, and the radiation therapy system is a neutron capture therapy system, more preferably, the neutron capture therapy system is an accelerator boron neutron capture therapy system.

The radiation therapy system and the support table disclosed in the invention are not limited to the contents described in the above embodiments and the structures shown in the drawings. Obvious variations, substitutions or modifications made to the materials, shapes and positions of the components therein on the basis of the invention, fall within the scope of the invention.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A radiation therapy system comprising:
   a radiation generation device configured to generate therapeutic radiation;
   an irradiation chamber configured to accommodate a to-be-irradiated object subjecting to irradiation of the radiation;
   a management chamber configured to perform irradiation control; and
   a support device configured to transport and support the to-be-irradiated object, wherein the support device comprises:
   a support member configured to support the to-be-irradiated object, wherein the support member comprises a first surface;
   an adjustment component configured to adjust a spatial position of the support member; and
   a clamping component configured to fixedly connect the support member and the adjustment component together in a detachable manner, wherein the clamping component comprises:
   a first positioning block disposed on the first surface of the support member,
   a second positioning block disposed on the adjustment component, and
   a locking member configured to lock or release the second positioning block relative to the first positioning block,
   wherein the first positioning block is provided with a limiting slot for the second positioning block to be inserted along a first direction parallel to the first surface, a reserved slot communicated with the limiting slot along a second direction perpendicular to the first surface such that the adjustment component passes through the reserved slot, and a locking hole located at a side of the limiting slot and communicated with the limiting slot, the locking hole is configured to be matched with the locking member along a locking direction perpendicular to the first direction and the second direction, the limiting slot penetrates through one of faces of the first positioning block along the first direction to form an insertion opening, and the second positioning block is inserted into the limiting slot from the insertion opening along the first direction.

2. The radiation therapy system according to claim 1, wherein the locking member comprises a mounting part fixedly connected with the second positioning block, a locking pin insertable into or movable out of the locking hole along the locking direction, and a first driving member configured to drive the locking pin to insert into or move out of the locking hole along the locking direction, and the locking hole penetrates through the first positioning block along the locking direction and communicates with the limiting slot.

3. The radiation therapy system according to claim 2, wherein the support device further comprises a detection component configured to detect whether the locking pin is moved in place so as to determine whether the support member and the adjustment component are effectively connected together.

4. The radiation therapy system according to claim 1, wherein the radiation therapy system further comprises a transmission device disposed between the adjustment component and the support member such that the support member is movable relative to the adjustment component.

5. The radiation therapy system according to claim 4, wherein the transmission device comprises a substrate fixedly connected with the adjustment component, a guiding member disposed on the substrate, a slider slidable relative to the guiding member, a driving block configured to drive the slider to move, and a second driving member configured to drive the driving block to move.

6. The radiation therapy system according to claim 1, wherein the radiation therapy system further comprises a positioning device configured to control a movement trajectory of the support member.

7. The radiation therapy system according to claim 6, wherein the positioning device comprises a laser positioning component, an alignment component, an optical verification component, a distance measuring component, a driving component configured to drive the adjustment component to move so as to drive the support member to move, and a control component configured to control a movement trajectory of the adjustment component.

8. The radiation therapy system according to claim 7, wherein the alignment component comprises a positioning frame with an adjustable relative position with respect to the support member, a support rod connected between the support member and the positioning frame to adjust the relative position of the positioning frame with respect to the support member, and a locking member configured to lock the relative position of the positioning frame with respect to the support member.

9. The radiation therapy system according to claim 8, wherein the irradiation chamber is provided with a collimator allowing emission of the radiation, the radiation emits from an exit of the collimator and defines a beam axis with an optimal treatment point, and the laser positioning component comprises at least two laser emitters disposed at different orientations, lasers emitted by the at least two laser emitters have a laser intersection point, and an optimal irradiation point of the to-be-irradiated object, the laser intersection point and the optimal treatment point coincide during treatment.

10. The radiation therapy system according to claim 9, wherein the positioning frame has a positioning point coinciding with the optimal irradiation point of the to-be-irradiated object during treatment.

11. The radiation therapy system according to claim 10, wherein the optical verification component comprises a CCD camera as well as an image processing and identifying module.

12. An operation procedure of the positioning device of the radiation therapy system according to claim 11, comprising:

S1: marking, by the laser positioning component, the optimal treatment point by using the laser intersection point, and the optimal treatment point corresponding to a coordinate (X, Y, Z) and a relative angle $\alpha$;

S2: taking, by the CCD camera, a picture of the laser intersection point to obtain a photo, and analyzing and marking, by the image processing and identifying module, the laser intersection point in the photo;

S3: locating the to-be-irradiated object on the support member, and aligning, by a medical staff, the positioning point of the positioning frame with the optimal irradiation point of the to-be-irradiated object, and then locking, by the medical staff, a position of the positioning frame by using the locking member;

S4: taking, by the CCD camera, a picture in which the to-be-irradiated object is located on the support member and the alignment component is adjusted in place to obtain a photo, then analyzing and recording, by the image processing and identifying module, a coordinate (X1, Y1) and a relative angle $\alpha1$ of a positioning point of the alignment component in the photo, and then calculating, by the image processing and identifying module, a coordinate difference value between the positioning point and the laser intersection point: X0=X1−X, Y0=Y1−Y, $\alpha0=\alpha1-\alpha$;

S5: determining, by the control component, the movement trajectory of the adjustment component through calculation according to the coordinate difference value obtained from the optical verification component, and then controlling, by the control component, the driving component to drive the adjustment component to move, such that the optimal irradiation point of the to-be-irradiated object on the support member is moved to a position corresponding to a coordinate (x, y) and the relative angle $\alpha$;

S6: detecting, by the distance measuring component, a distance between the positioning point and the laser intersection point; and S7: determining, by the control component, the movement trajectory of the adjustment component through calculation according to data obtained from the distance measuring component, and then controlling, by the control component, the drive component to drive the adjustment component to move, such that the optimal irradiation point of the to-be-irradiated object on the support member is moved to the optimal treatment point, that is, a position corresponding to the coordinate (X, Y, Z) and the relative angle $\alpha$, for treatment.

13. An operation procedure of the positioning device of the radiation therapy system according to claim 11, comprising:

S1: marking, by the laser positioning component, the optimal treatment point by using the laser intersection point, and the optimal treatment point corresponding to a coordinate (X, Y, Z) and a relative angle $\alpha$;

S2: taking, by the CCD camera, a picture of the laser intersection point to obtain a photo, and analyzing and marking, by the image processing and identifying module, the laser intersection point in the photo;

S3: locating the to-be-irradiated object on the support member, and aligning, by a medical staff, the positioning point of the positioning frame with the optimal irradiation point of the to-be-irradiated object, and then locking, by the medical staff, a position of the positioning frame by using the locking member;

S4: taking, by the CCD camera, a picture in which the to-be-irradiated object is located on the support member and the alignment component is adjusted in place to obtain a photo, then analyzing and recording, by the image processing and identifying module, a coordinate (X1, Y1) and a relative angle $\alpha 1$ of a positioning point of the alignment component in the photo, and then calculating, by the image processing and identifying module, a coordinate difference value between the positioning point and the laser intersection point: $X0=X1-X$, $Y0=Y1-Y$, $\alpha 0=\alpha 1-\alpha$;

S5: detecting, by the distance measuring component, a distance between the positioning point and the laser intersection point; and S6: determining, by the control component, the movement trajectory of the adjustment component through calculation according to data obtained from the optical verification component and the distance measuring component, and then controlling, by the control component, the driving component to drive the adjustment component to move, such that the optimal irradiation point of the to-be-irradiated object on the support member is moved to the optimal treatment point, that is, a position corresponding to the coordinate (X, Y, Z) and the relative angle $\alpha$.

14. The radiation therapy system according to claim 1, wherein the support member is selected from multiple types of support members having different shapes and sizes, and the multiple types of support members comprise:

a first support member, being plate-shaped; and a second support member, being chair-shaped.

* * * * *